(12) United States Patent　　(10) Patent No.: US 9,943,819 B2
Sidhu　　(45) Date of Patent: Apr. 17, 2018

(54) SMALL-SCALE REACTOR HAVING IMPROVED MIXING

(71) Applicant: Singh Instrument LLC, Fremont, CA (US)

(72) Inventor: Robbie Singh Sidhu, Fremont, CA (US)

(73) Assignee: Singh Instrument LLC, Fremont, CA (US)

( * ) Notice: Subject to any disclaimer, the term of this patent is extended or adjusted under 35 U.S.C. 154(b) by 91 days.

(21) Appl. No.: 14/931,403

(22) Filed: Nov. 3, 2015

(65) Prior Publication Data

US 2016/0121290 A1　　May 5, 2016

Related U.S. Application Data

(60) Provisional application No. 62/074,358, filed on Nov. 3, 2014.

(51) Int. Cl.
　　*B01J 8/10*　　(2006.01)
　　*G01N 31/10*　　(2006.01)
　　*B01J 19/00*　　(2006.01)
　　*B01F 11/00*　　(2006.01)

(52) U.S. Cl.
　　CPC ............ *B01J 8/10* (2013.01); *B01F 11/0054* (2013.01); *B01J 19/0066* (2013.01); *G01N 31/10* (2013.01); *B01J 2208/00814* (2013.01); *B01J 2208/00858* (2013.01); *B01J 2208/00876* (2013.01); *B01J 2208/00911* (2013.01);
(Continued)

(58) Field of Classification Search
　　CPC ................. B01J 8/10; B01J 19/0066; B01J 2208/00814; B01J 2208/00858; B01J 2208/00876; B01J 2208/028; B01F 11/0054
See application file for complete search history.

(56) References Cited

U.S. PATENT DOCUMENTS 3,431,077 A　　3/1969　Danforth
3,536,452 A　　10/1970　Norton
(Continued)

FOREIGN PATENT DOCUMENTS

EP　　0796654　　9/1997
GB　　967261　　8/1964
WO　　9615576　　5/1996

OTHER PUBLICATIONS

Burns, "Development of a Microreactor for Chemical Production", Process Miniaturization: 2nd Int'l Conference on Microreaction Technology, Mar. 9-12, 1998, New Orleans, LA, pp. 39-44.
(Continued)

*Primary Examiner* — Lessanework Seifu
(74) *Attorney, Agent, or Firm* — Senniger Powers LLP

(57) ABSTRACT a reactor for conducting laboratory reactions comprises includes reaction vessel, a catalyst holder in the reaction vessel, and a drive system configured to drive reciprocating linear movement of the catalyst basket. The catalyst holder can be configured to hold a plurality of catalyst particles so the catalyst particles remain spaced apart from one another. A reactor for conducting laboratory reactions can also include a reaction vessel, an impeller in the reaction vessel, and a drive system configured to drive reciprocating linear movement of the impeller.

19 Claims, 15 Drawing Sheets

(52) U.S. Cl.
CPC .............. *B01J 2208/028* (2013.01); *B01J 2219/00011* (2013.01); *B01J 2219/00779* (2013.01)

(56) References Cited

U.S. PATENT DOCUMENTS

| | | | |
|---|---|---|---|
| 3,767,535 A * | 10/1973 | Havewala | .............. B01J 8/10 366/328.2 |
| 4,061,870 A | 12/1977 | Mizushina | |
| 4,099,923 A | 7/1978 | Milberger | |
| 4,169,681 A * | 10/1979 | Kato | .............. B01F 11/0054 366/244 |
| 4,511,412 A * | 4/1985 | Kakino | .............. B01F 3/0807 149/109.6 |
| 4,670,404 A | 6/1987 | Swift | |
| 4,705,669 A | 11/1987 | Tsuji | |
| 4,923,306 A | 5/1990 | Fauske | |
| 5,229,075 A | 7/1993 | Fauske | |
| 5,304,354 A | 4/1994 | Finley | |
| 5,324,483 A | 6/1994 | Cody | |
| 5,417,938 A | 5/1995 | Shelden | |
| 5,534,328 A | 7/1996 | Ashmead | |
| 5,547,282 A | 8/1996 | Pinhack | |
| 5,580,523 A | 12/1996 | Bard | |
| 5,589,136 A | 12/1996 | Northrup | |
| 5,593,642 A | 1/1997 | DeWitt | |
| 5,595,712 A | 1/1997 | Harbster | |
| 5,603,351 A | 2/1997 | Cherukuri | |
| 5,611,214 A | 3/1997 | Wegeng | |
| 5,639,423 A | 6/1997 | Northrup | |
| 5,658,537 A | 8/1997 | Dugan | |
| 5,690,763 A | 11/1997 | Ashmead | |
| 5,811,062 A | 9/1998 | Wegeng | |
| 5,843,385 A | 12/1998 | Dugan | |
| 5,866,342 A | 2/1999 | Antonenko | |
| 6,132,686 A | 10/2000 | Gallup | |
| 6,149,882 A | 11/2000 | Guan | |
| 6,157,009 A | 12/2000 | Fauske | |
| 6,175,409 B1 | 1/2001 | Nielsen | |
| 6,306,658 B1 | 10/2001 | Turner | |
| 6,406,632 B1 | 6/2002 | Safir | |
| 6,489,168 B1 | 12/2002 | Wang | |
| 6,556,940 B1 | 4/2003 | Tretiakov | |
| 6,616,909 B1 | 9/2003 | Tonkovich | |
| 6,667,009 B1 | 12/2003 | Desrosiers | |
| 6,680,044 B1 | 1/2004 | Tonkovich | |
| 6,701,774 B2 | 3/2004 | Srinivasan | |
| 6,737,026 B1 | 5/2004 | Bergh | |
| 6,818,183 B2 | 11/2004 | Hajduk | |
| 6,869,799 B1 | 3/2005 | Guan | |
| 7,021,820 B2 | 4/2006 | Chippett | |
| 8,460,615 B2 * | 6/2013 | Persson | .............. B01F 7/00033 210/683 |
| 2002/0042140 A1 | 4/2002 | Hagemeyer | |
| 2002/0085446 A1 | 7/2002 | Van Den Brink | |
| 2003/0190260 A1 | 10/2003 | Wheeler | |
| 2004/0141893 A1 | 7/2004 | Martin | |
| 2005/0009175 A1 | 1/2005 | Bergh | |
| 2005/0175519 A1 | 8/2005 | Rogers, Jr. | |
| 2005/0232074 A1 | 10/2005 | Higashihara | |

OTHER PUBLICATIONS

Franz, "New Operating Regimes and Applications Feasible with Microreactors", MIT, 1997, pp. 33-38.
Greenway, "The Use of Novel Microreactor for High Throughput Continuous Flow Organic Synthesis", Sensors and Actuators B, vol. 63, 2000, pp. 153-158.
Haswell, "The Application of Micro Reactors to Synthetic Chemistry", Chem. Commun., 2001, pp. 391-398.
Jackel, "Microtechnology: Application Opportunities in the Chemical Industry", Dechema Monographs, vol. 132, 1996, pp. 29-50.
Johansson, "Nanofabrication of Model Catalysts and Simulations of Their Reaction Kinetics", J. Vac. Sci. Technol. A, vol. 17, No. 1, Jan./Feb. 1999, pp. 297-302.
Klein, "Combinatorial Material Libraries on the Microgram Scale with an Example of Hydrothermal Synthesis", Angew. Chem. Int. Ed., vol. 37, No. 24, 1998, pp. 3369-3372.
Lowe, "Microreactor Concepts for Heterogeneous Gas Phase Reactions", Process Miniaturization: 2nd Int'l. Conference on Microreaction Technology, Mar. 9-12, 1998, New Orleans, LA, pp. 63-73.
Matlosz, "Microsected Electrochemical Reactors for Selective Partial oxidation", Process Miniaturization: 2nd Int'l. Conference on Microreaction Technology, Mar. 9-12, 1998, New Orleans, LA, pp. 54-59.
Perez-Ramirez, "The Six-Flow Reactor Technology: A Review on Fast Catalysis Screening and Kinetic Studies", Catalysis Today, vol. 60, 2000, pp. 93-109.
Sie, "Miniaturization of Hydroprocessing Catalyst Testing Systems: Theory and Practice", AIChE Journal, vol. 42, No. 12, Dec. 1996, pp. 3498-3507.
Srinivasan, "Micromachined Reactors for Catalytic Partial Oxidation Reactions", AIChE Journal, vol. 43, No. 11, Nov. 1997, pp. 3059-3069.
Tonkovich, "The Catalytic Partial Oxidation of Methane in a Microchannel Chemical Reactor", Process miniaturization: 2nd Int'l. Conference on Microreaction Technology, Mar. 9-12, 1998, New Orleans, LA, pp. 45-53.
Weissmeier, "Strategy for the Development of Micro Channel Reactors for Heterogenously Catalyzed Reactions", in Ehrfeld, Rinard, Wegner (Eds.) Process Miniaturization: 2nd International Conference on Microreaction Technology, IMRET 2, Topical Conference Preprints, pp. 24-32, AIChE, New Orleans (1998).
Zech, "Simultaneous Screening of Catalysts in Microchannels: Methodology and Experimental Setup" Ehrfeld and Wolfgang (Eds.), Springer-Verlag, Berlin, Germany, Proceedings of the Int'l. Conference on Microreaction Technology, 1999, pp. 260-266.
Zieren, "Time-Resolved Calorimetry in a New Type of Micro Fluid Reactor Using Specially Separated Thin-Film Themnoppiles and FIA-Technique", Process Miniaturization: 2nd Int'l Conference on Microreaction Technology, Mar. 9-12, 1998, New Orleans, LA, pp. 154-163.
Dyer, "Scale-Up of a Vilsmeier Formylation Reaction: Use of HEL Auto-MATE and Simulation Techniques for Rapid and Safe Transfer to Pilot Plant from Laboratory", Organic Process Research & Development, 2002, pp. 311-316, vol. 6 No. 3.
"Parr Calorimetry Methods and Modes", http://www.parrinst.com/default.cfm?page_ID=183, May 22, 2008, 2 pgs.
"Parr Calorimeter Selection", http://www.parrinst.com/default.cfm?page_ID=2-5, May 22, 2008, 6 pgs.
":reactor systems Parallel Process Optimisation", http://helgroup.com/home/ractor-systems/parallelprocessopt.html?subpage+3; Oct. 2, 2008, 2 pgs.
Simms, "Rapid Process Development and Scale-Up Using a Multiple Reactor System", Organic Process Research & Development, 2000, 9 pgs.
Singh, Parallel Synthesis of High Pressure Reactions—including catalyst development, date unknown, 9 pgs.
Steininger, "Four-Reactor Apparatus for Chromatographic Studies of Catalysts and Sorbents", Journal of Chromatography,1982, 279-284, 243, Elsevier Scientific publishing Company, Amsterdam, Netherlands.
Wingaarden (Ed.), Industrial Catalysis-Optimizing Catalysts and Processes, 1998, Wiley-VCH Verlag GmbH, Weinheim, 99 pgs.

* cited by examiner

FIG. 8
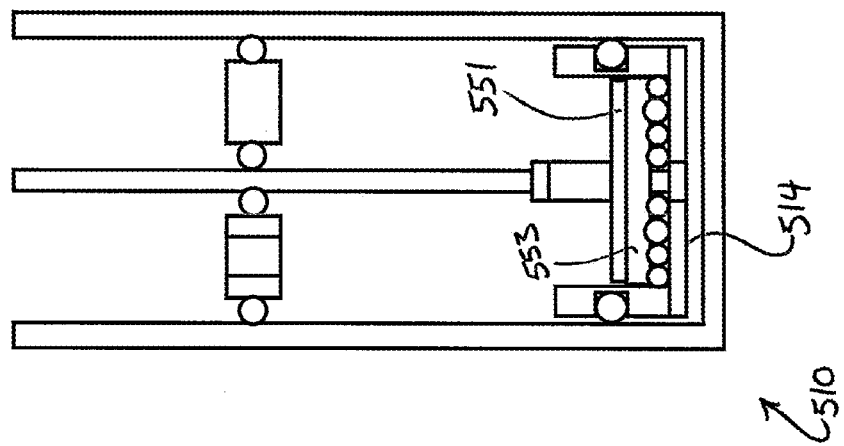
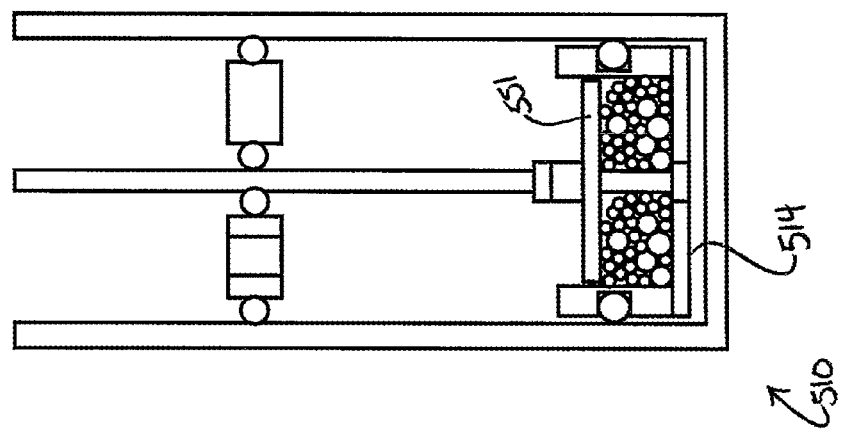

SMALL-SCALE REACTOR HAVING IMPROVED MIXING

CROSS REFERENCE TO RELATED APPLICATION

This application claims priority to U.S. Provisional Patent Application Ser. No. 62/074,358, filed on Nov. 3, 2014, which is hereby for all purposes incorporated by reference.

FIELD OF THE INVENTION

The present invention relates generally to small-scale (e.g., laboratory and/or bench top) reactor systems used to research chemical reactions, and more particularly to methods and apparatus for mixing reaction materials in small-scale reactor systems.

BACKGROUND

Small-scale laboratory reactors are commonly used to explore and conduct research into topics of interest associated with chemical reactions. Many different types of experiments can be performed to study reaction materials, reaction variables, processes associated with chemical reactions, and other aspects of chemical reactions. Reaction materials include chemical reagents, catalysts, catalyst promoters, catalysts inhibitors, catalyst supports, and reaction products. For example research may be conducted into factors that may affect the desirability and/or economic viability of using particular reaction materials, process variables, and/or manufacturing techniques to carry out commercially significant chemical reactions.

Many chemical reactions require or can be facilitated by presence of a catalyst in a reaction vessel. As is generally known, a catalyst is a substance that can facilitate a chemical reaction without itself being consumed in the reaction. Typically, a catalyst must come into contact with one or more of the chemical reagents to catalyze the reaction. Heterogeneous catalysts are in a different phase than the chemical reagents. Most heterogeneous catalysts are solid phase and act on liquid and/or gaseous reagents. One common technique for conducting reactions involving a heterogeneous catalyst is to place a porous catalyst basket inside a reaction vessel containing liquid and/or gaseous reagents. The catalyst is placed in the catalyst basket before the reaction is started.

The catalyst is typically dispersed on the surface of a catalyst support, such as pellets made of a zeolite or other suitable porous material. The catalyst support pellets form a catalyst bed in the catalyst basket. The basket is at least partially porous so the fluid reagents can pass through the basket and contact the catalyst in the basket. But the pores or openings in the basket are small enough to retain the catalyst support pellets in the basket. Thus, the catalyst is generally confined to the catalyst basket.

During the reaction, a mixing system may be used to mix the reagents and produce flow of the reagents through the catalyst bed. One type of mixing system includes a rotating stirrer (e.g., impeller) that stirs liquid phase reaction materials. The catalyst basket can remain stationary as the stirrer causes fluid reagents to flow radially outward through the catalyst bed. One example of this is in U.S. Pub. Application No. 20040042942. Another type of mixing system rotates the catalyst basket in the reaction vessel. The rotating basket performs the function of an impeller and stirs the fluid reagents while generating flow of fluid reagents through the catalyst bed in the basket.

Currently used reactors having catalysts baskets are often unable to obtain good gas-liquid mass transfer, particularly in relatively smaller-sized reactors (e.g., reactors having an internal volume less than about 2500 mL. In smaller-sized reactors the impellers need to be designed to allow for the physical presence of the catalyst baskets. The catalyst baskets also must be designed to hold a sufficient volume of catalyst. Consequently, because of the limited amount of space inside smaller-sized reactors, the effective blade diameter of the impellers is much less than ideal for generating good KLa values.

In order to obtain decent KLa values in smaller-sized reactors, high rotational rates for the baskets/impellers are required. However, shear forces increase as the speed of rotation is increased. In conventional reactors having catalyst baskets, the increased shear forces can degrade larger catalyst particles, generating fines. Fines are undesirable because they make results difficult to interpret during characterization of the system because the experiments are designed to study the intrinsic activity of the catalyst on large catalyst particles. When high speed rotary agitation is introduced to increase mass transfer, fine particles are generated and the reaction is a combination of slurry and large particle catalyst. The inability to achieve good KLa values in smaller-sized reactors sometimes leads scientists to conduct tests in larger reactors that more closely resemble a pilot reactor or production reactor. However, larger reactors require more materials and longer setup times. This is more expensive and increases the time required to bring new products to market.

Also, when there are both gas and liquid phase reagents it can be difficult to achieve good mixing of the gas and liquid phase materials in a reactor having a catalyst basket. The catalyst basket is typically at least partially immersed in the liquid phase. The conventional mixing systems direct liquid flow radially outward through the catalyst bed. Flow of the liquid phase in a radial direction does little to mix the gaseous phase into the liquid. In some cases the conventional catalyst basket can impede mixing of gas and liquid phase reagents, particularly to the portion of the liquid phase below the basket.

The inventor has developed improved systems and methods for mixing reaction materials in a laboratory reactor system, which will be described in detail below.

SUMMARY

In one aspect, a reactor for conducting laboratory reactions comprises a reaction vessel, a catalyst basket in the reaction vessel, and a drive system configured to drive reciprocating linear movement of the catalyst basket.

In another aspect, a reactor for conducting laboratory reactions comprises a reaction vessel and a catalyst holder in the reactor. The catalyst holder is configured to hold a plurality of catalyst particles so the catalyst particles remain spaced apart from one another.

In another aspect, a reactor for conducting laboratory reactions comprises a reaction vessel, an impeller in the reaction vessel, a drive system configured to drive reciprocating linear movement of the impeller. Other aspects and features will also be apparent hereinafter.

BRIEF DESCRIPTION OF THE DRAWINGS

FIG. 8 is schematic diagram illustrating another embodiment of a reactor of the present invention;

Corresponding features are given corresponding reference numbers throughout the drawings.

DETAILED DESCRIPTION

Figure 1:
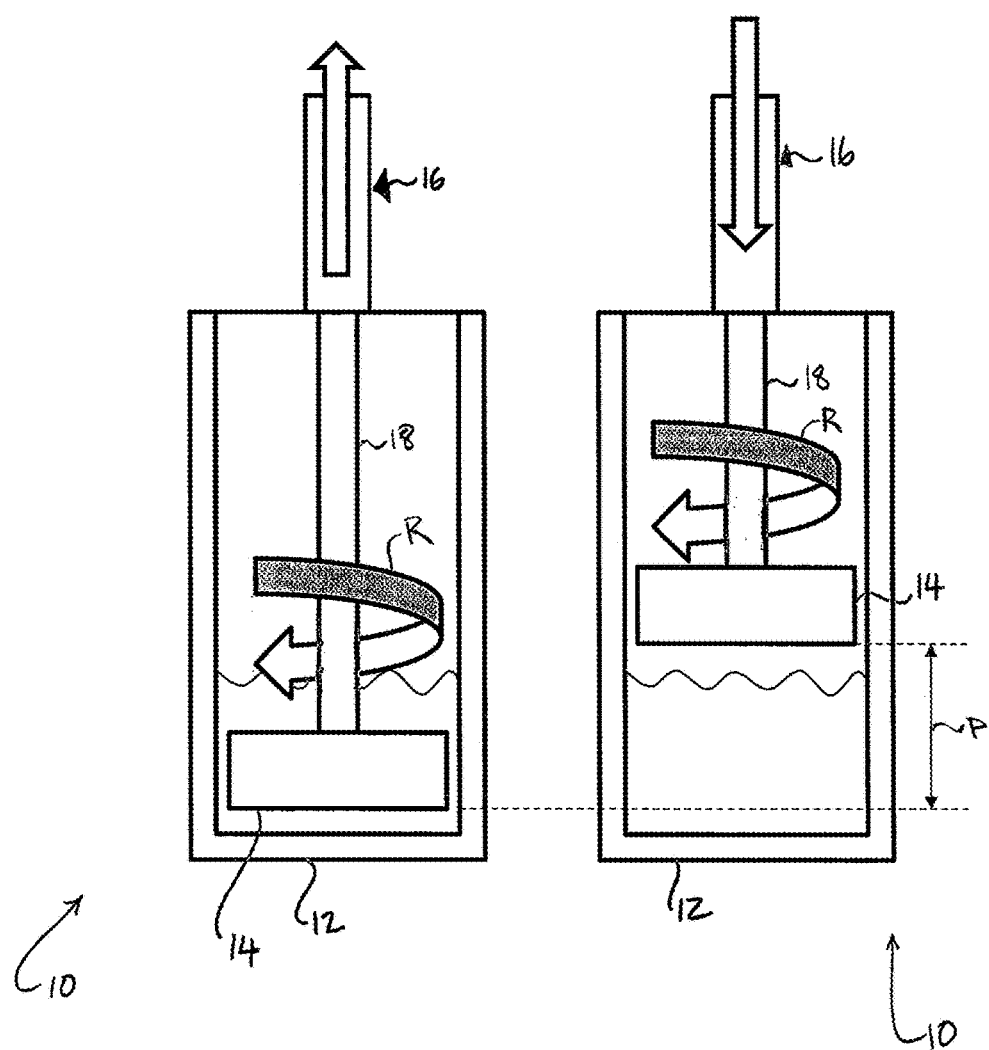
FIG. 1 is a schematic diagram illustrating one embodiment of a reactor of the present invention.

Referring now to the drawings, first to FIG. 1, one embodiment of a reactor is generally indicated at reference numeral 10. The reactor 10 includes a reaction vessel 12, a catalyst basket 14 (broadly a catalyst holder), and a mixing system 16 (broadly, a drive system) connected to the catalyst basket for driving motion of the catalyst basket.

The reaction vessel 12 can be any container suitable for containing the reaction materials involved in a reaction of interest. The reaction vessel 12 may be a vial, pressure vessel, well, or other structure capable of containing liquids, slurries, or other non-gaseous materials. The reaction vessel 12 may be sealed (e.g., include a head) to contain gaseous reaction mixtures. Moreover, the reaction vessel 12 can include one or more inlets (e.g., to provide gaseous and/or liquid feedstock) and/or outlets (e.g., to regulate pressure and/or evacuate reaction products or byproducts during a reaction). The reaction vessel 12 can be a stand-alone system or it can be one of an array of reaction vessels. Although the volume of the reaction vessel 12 may vary within the scope of the invention, the reaction vessel is suitably a relatively small-scale reaction vessel to facilitate running multiple different experiments using a relatively small amount of reaction materials. For example, the internal volume of the reaction vessel 12 is suitably in the range of about 1 mL to about 50 L, more suitably in the range of about 10 mL to about 5 L, and still more suitably in the range of about 20 mL to about 500 mL.

Figure 2:
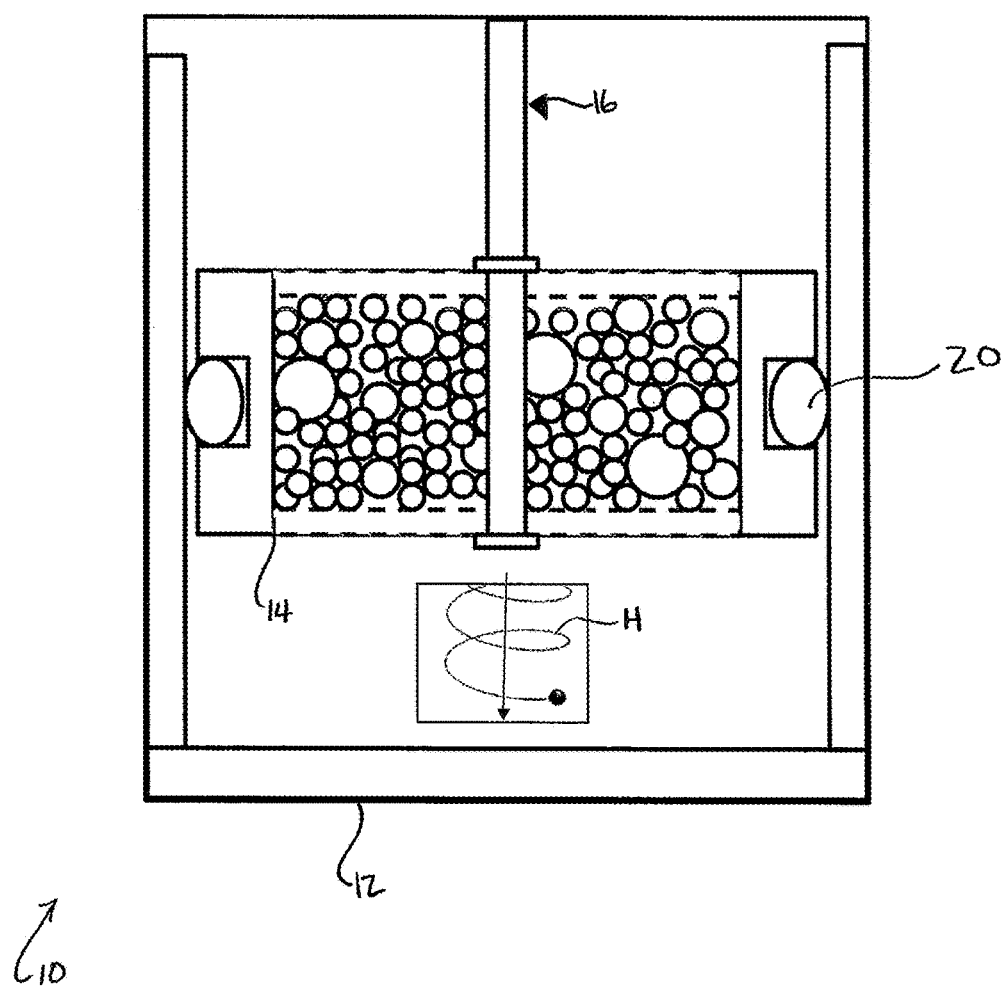
FIG. 2 is a schematic diagram of the reactor illustrated in FIG. 1 showing one embodiment of a catalyst basket for use in the reactor in more detail.

The catalyst basket 14 can be any structure suitable for containing a catalyst. As illustrated in FIG. 2, for example, the catalyst basket 14 is configured to enclose a space for holding catalyst particles within a cylindrical sidewall and circular top and bottom walls. At least some parts of the basket 14 are permeable to liquid and/or gas. As illustrated in FIG. 2, the top and bottom walls are made of a material that is permeable to liquid and gaseous reaction materials. For example, the top and bottom walls are suitably made of a metal mesh or porous metal material having pores or openings large enough to accommodate flow of liquid and gas therethrough, but small enough to contain catalyst particles within the enclosed space. The volume of the space enclosed by the catalyst basket 14 can vary within the broad scope of the invention. However, it can be desirable for the catalyst basket 14 to be relatively small to facilitate experiments using small amounts of catalyst and other reaction materials. For instance, the catalyst basket 14 is suitably designed to contain between about 0.1 mL to about 5 L, more suitably between about 0.5 mL to about 300 mL, and still more suitably between about 1 mL and about 30 mL.

The catalyst basket 14 is drivingly connected to a drive system configured to move the catalyst basket within the reaction vessel 12. In FIGS. 1 and 2, the drive system 16 includes a spindle 18 connected to the basket 14. The drive system 16 is suitably configured to drive the catalyst basket 14 to rotate in a direction R and also to reciprocate along a linear path P, as illustrated schematically in FIG. 1. For example, the drive system 16 can suitably drive the catalyst basket 14 to rotate on the axis of the spindle 18 and simultaneously reciprocate along a linear path P (e.g., a substantially vertical path) parallel to the spindle. The result of rotation and simultaneous linear movement is a helical path H, as shown in FIG. 2. Accordingly, the drive system 16 is suitably configured to drive the catalyst basket 14 along a helical path H, meaning points on the catalyst basket that are not on the axis of rotation move in a helical path as the drive system simultaneously drives rotation and linear movement of the catalyst basket, as illustrated in FIG. 2.

The drive system 16 is suitably configured to drive the rotation of the catalyst basket 14 at a relative slow speed. For example, the drive system 16 is suitably configured to rotate the catalyst basket 14 at a speed in the range of 0 rpm to about 600 rpm. As noted by the low end of the range, in some cases it may be desirable to rotate the catalyst basket 14 at a very low speed or not at all. In contrast, some conventional reactors that use pure rotary motion have to drive rotating catalyst baskets at speeds as high as 2,000 rpm to achieve adequate mass transfer rates. The reactor 10 is also configured to achieve desired high mass transfer rates while maintaining relatively low shear conditions in the catalyst bed. During high speed rotation of a catalyst basket in conventional reactors shear forces (which increase as the speed of rotation is increased) degrade larger catalyst particles, generating so-called fines. Fines are undesirable because the can make results difficult to interpret. When high speed rotary agitation is introduced to obtain good gas-liquid mass transfer, fine particles are generated and the reaction is a combination of slurry and large particle catalyst. However, it is often desirable to study the intrinsic activity of the catalyst on large catalyst particles in which case the production of fines introduces an unwanted variable. The reactor 10 described herein advantageously allows relatively high mass transfer rates in the range of about 0.1 to about 1.2 $S^{-1}$ while at the same time limiting shear forces acting on the catalyst particles and thereby reducing the number of fines produced. In some cases production of fines can be substantially eliminated.

The drive system 16 is suitably operable to adjust the pitch of the helical path H by changing the ratio of the angular velocity relative to the linear velocity. For example, the drive system 16 is suitably operable to drive the catalyst basket 14 at an angular velocity in the range of about 0 rpm to about 600 rpm and to simultaneously drive the catalyst basket 14 to move at a maximum linear velocity in the range of 0 to 1.0 m/s. It is understood that the linear velocity may vary depending on the linear position of the basket 14 on its reciprocating path P. In some cases it may be desirable to drive linear movement of the catalyst basket 14 according to a harmonic oscillation, such as by using a Scotch Yoke to convert rotary movement to sinusoidal reciprocating movement. The frequency of the linear oscillatory component of the motion is suitably in the range of about 1 Hz to about 10 Hz.

The reactor 10 is suitably configured to drive flow of fluid reaction materials through the catalyst basket 14 in a direction that includes a non-radial direction. The reactor 10 is also configured to drive fluid reaction materials through all parts of a catalyst bed that occupies substantially all of the cross sectional area of the reactor vessel 12 at the position of the catalyst basket 14. This is in contrast to conventional reactors that use simple rotary motion (of a catalyst basket or stirrer) to produce flow of reaction materials through a catalyst bed. In the case of simple rotary motion, fluids are driven radially outward through the catalyst bed until they reach a point at which they either exit the catalyst bed (in the case of a gap between the catalyst bed and the reactor sidewall) or are forced in a vertical direction by the reactor sidewall or another barrier to infinite flow in the radial direction. This radial flow tends to result in stagnation of fluid flow at various locations in the catalyst bed.

The reactor 10 is suitably configured so the catalyst basket 14 divides the internal space of the reactor into different zones. As illustrated in FIG. 2, for example, the catalyst basket 14 is sealed against the internal sidewall of the reactor vessel 12 (e.g., by an O-ring 20) to limit flow of reaction materials between a zone below the catalyst basket and a zone above the catalyst basket. The seal between the catalyst basket 14 and the reactor sidewall limits the amount of material that can flow between the upper and lower zones without flowing through the porous catalyst basket. This can enhance flow of reaction materials through the bed of particles in the catalyst basket 14. Referring to FIG. 2, which illustrates the catalyst basket 14 in the midst of a downstroke for example, the reactor 10 is configured so the linear reciprocating motion of the catalyst basket changes the volumes of the upper and lower zones defined by the catalyst basket. There will commonly be substantially incompressible liquid reaction materials in the lower zone of the reactor 10, in which case the downward movement of the catalyst basket 14 forces liquid reaction materials to flow through the bed of particles in the catalyst basket. Even if there are compressible gaseous reaction materials in the upper and lower zones of the reactor 10, the reciprocating linear movement of the catalyst basket 14 combined with the seal between the catalyst basket and the reactor sidewall will produce alternating pressure differentials across the catalyst basket that will drive reaction materials (gaseous and/or liquid) through the porous catalyst basket.

The reactor 10 is configured to allow users to select multiple different operating modes by adjusting the level of liquid reaction materials in the reactor 10 relative to the catalyst basket 14. In particular, the way the bed of catalyst materials in the catalyst basket 14 interacts with the reaction materials depends on the level of the liquid reaction materials relative to the upper and lower extremes of the reciprocating linear motion of the catalyst basket. For example, if the liquid level is high enough that the catalyst basket 14 is completely submerged throughout the reciprocating linear cycle, the reactor 10 operates as a submerged bed reactor 10. On the other hand, if the liquid level is lower than the catalyst basket 14 throughout the reciprocating linear cycle, the reactor 10 operates as a trickle bed reactor. Moreover, if the liquid level is between the upper and lower extremes of the linear reciprocating movement of the catalyst basket 14, the reactor 10 operates as a hybrid between a submerged bed reactor and a trickle bed reactor as the catalyst basket is repeatedly submerged in and then withdrawn from the liquid reaction materials. Accordingly, the mode in which the reactor 10 operates can be selected by adjusting the volume of liquid reaction materials in the vessel 12 and/or by adjusting the position of the catalyst basket 14 relative to the rest of the reactor.

Figure 3:
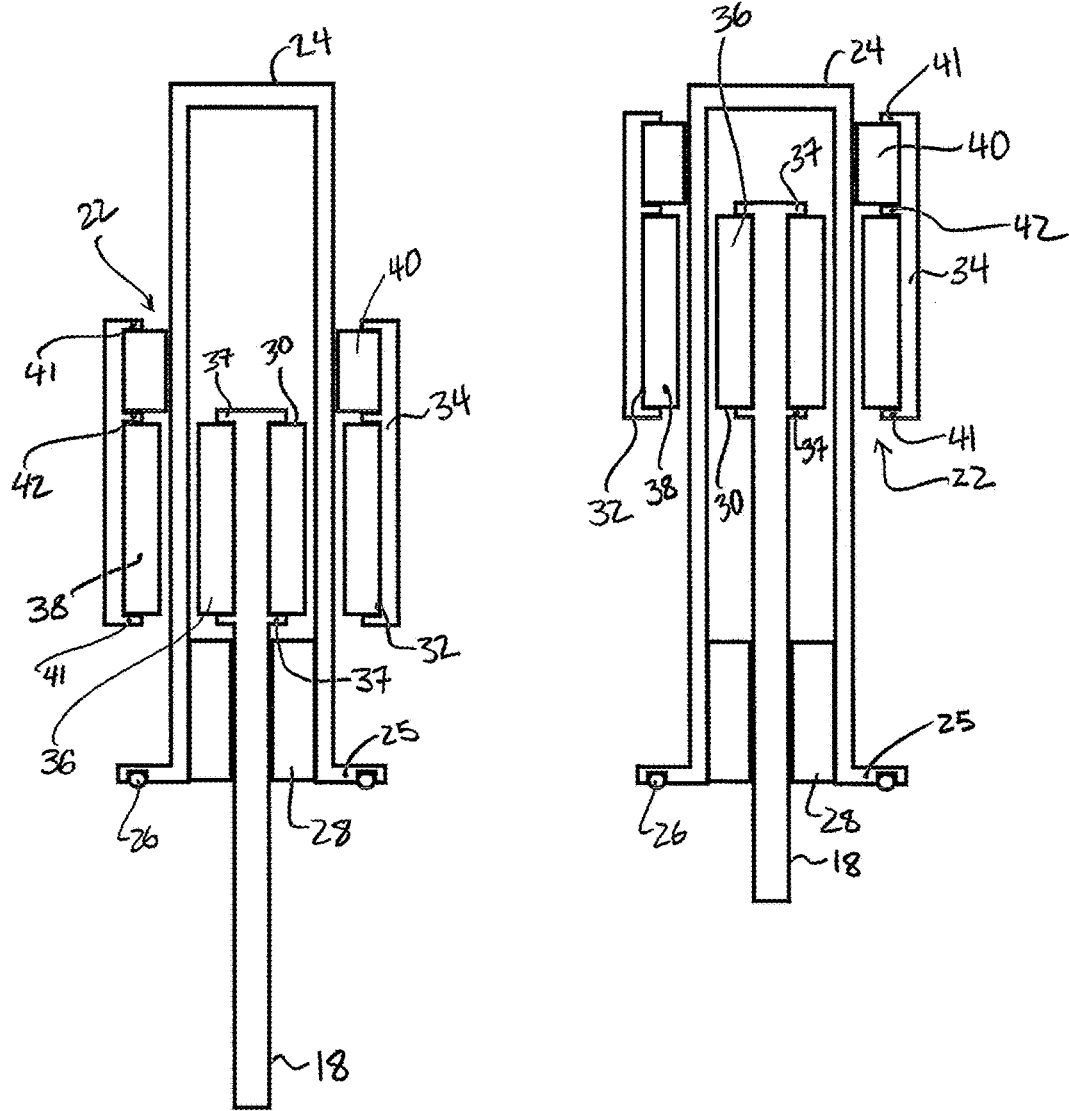
FIG. 3 is a schematic diagram of one embodiment of a magnetic coupling for use in the reactor illustrated in FIGS. 1 and 2.

FIG. 3 illustrates one embodiment of a magnetic coupling 22 that can be used to drive linear oscillatory and rotary motion of the spindle 12, and thereby drive the corresponding motions of the catalyst basket 14. The coupling 22 includes a pressurizable casing 24 configured to receive the upper end of the spindle 12 and to allow linear oscillatory movement of the upper end of the spindle within the casing. The casing 24 has closed end and an open end opposite the closed end. A flange 25 extends radially outward at the open end. A groove in the flange receives an O-ring 26 for forming a seal with the upper portion of the reactor vessel 12. The casing 24 suitably has a substantially cylindrical sidewall having a circular cross sectional shape. The sidewall suitably has a substantially uniform thickness and substantially cylindrical inner and outer surfaces. A bearing 28 is mounted at the open end of the casing 24. The bearing 28 suitably allows linear movement of the spindle 18 relative to the bearing while also allowing rotary movement of the spindle relative to the bearing. The spindle 18 extends through the bearing into the casing 24.

A magnetic follower 30 is secured to the spindle inside the casing. A magnetic driver 32 is secured to a carriage 34 outside the casing 24. Together, the magnetic follower 30 and the magnetic driver 32 form the magnetic coupling 22. In general, any structural arrangement having the capability of producing a linear oscillatory and rotational movement of the magnetic follower 30 using magnetic attraction and/or magnetic repulsion forces associated with movement of the magnetic driver 32 can be used within the broad scope of the invention.

In FIG. 3 for instance, one or more magnets 36 are suitably secured to the upper end of the spindle 18 in the casing 24 so linear and rotational movements of the magnets relative to the spindle are limited to constitute the magnetic follower. As illustrated in FIG. 3, the one or more magnets 36 are secured on the end of the spindle 18 between a pair of retainers 37 extending outward from the spindle that limit linear movement of the magnet(s) relative to the spindle. The retainers 37 can suitably be annular flanges extending radially outward from the spindle 18, but other structures can be used instead. Adhesive or other suitable fasteners can be used to limit rotational movement of the magnet(s) relative to the spindle. One or more splines (not shown) can also be included on the magnets and/or on the spindle to engage one or more grooves in the other of the magnets and the spindle to limit rotation of the magnets relative to the spindle. The magnets 36, bearing 28, and spindle 18 are arranged so the bearing maintains spatial separation between the magnets of the magnetic follower 30 and the inner surface of the sidewall of the casing 24.

The magnetic driver 32 in the embodiment illustrated in FIG. 3 includes one or more magnets 38 secured to the carriage 34 (e.g., by adhesive or any suitable fasteners). A bearing 40 is secured to an inner surface of the carriage 34. The casing 24 extends through the bearing 40 so the bearing is positioned between the outer surface of the casing and the carriage 34. The bearing 40 connecting the casing 24 to the carriage 34 is suitably substantially similar to the bearing 28 connecting the spindle 18 to the casing in that it allows both rotational and linear motion of the carriage relative to the casing. The magnets 38, carriage 24, and bearing 40 are arranged so the bearing maintains spatial separation between the magnets of the magnetic driver 32 and the outer surface of the sidewall of the casing 24. The carriage 34 can have variety of configurations within the broad scope of the invention. For example, the carriage 34 is suitably a substantially cylindrical sleeve having radially inwardly extending retainers 41 at its opposite open ends. The retainers 41 can be radially inwardly extending annular flanges, for instance. The carriage 34 suitably also includes one or more retainers 42 extending between the bearing 40 and the magnets 38 of the magnetic driver 32, as illustrated. This retainer 42 is also suitably a radially inwardly extending annular flange, although other configurations are also possible.

Figure 11:
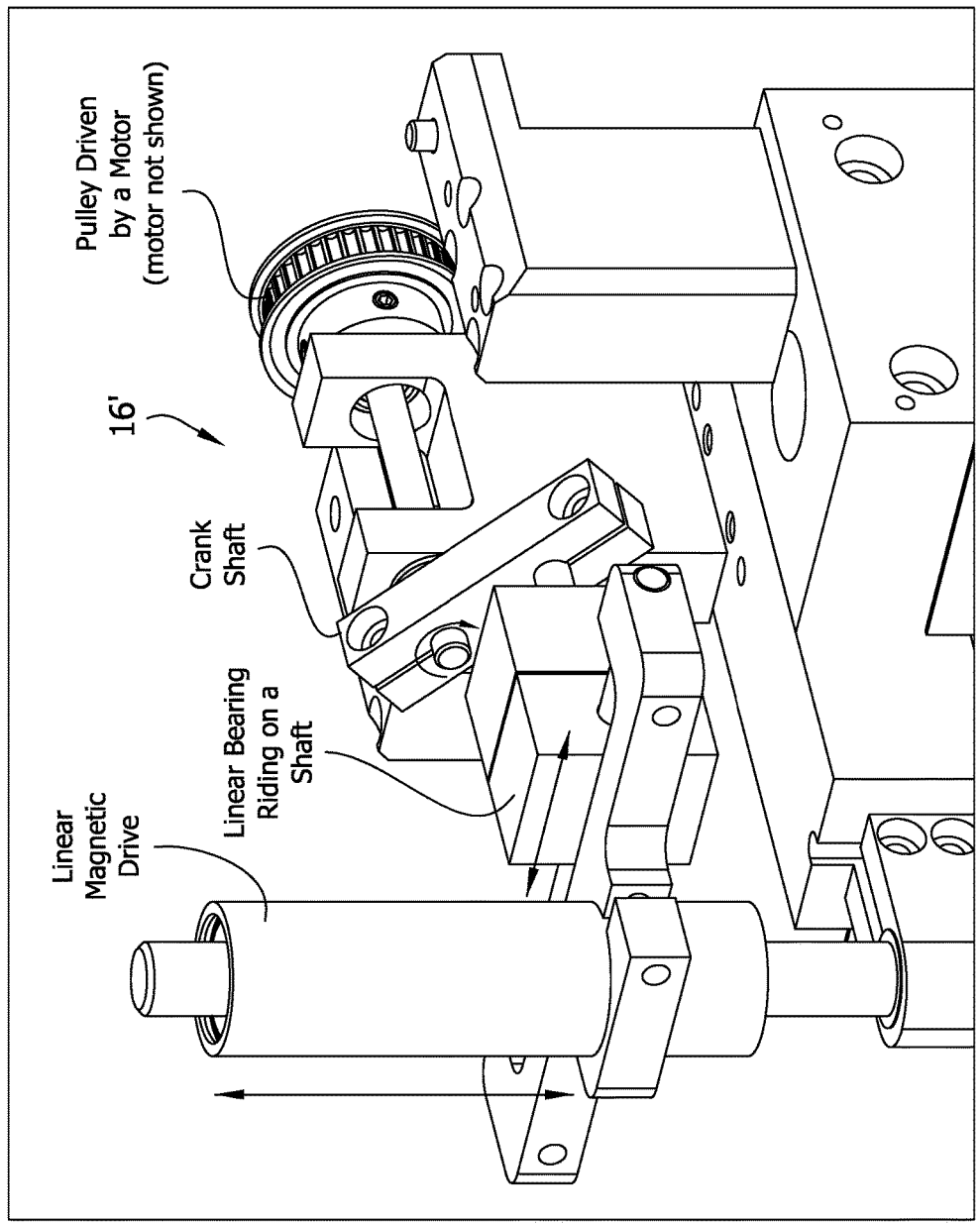
FIG. 11 is a photograph of one embodiment of a drive system having and adjustable crank arm that allows adjustment to the amplitude of reciprocal linear motion.

The carriage 40 is connected to a drive mechanism (not shown in FIG. 3) configured to drive rotational movement of the carriage about an axis coincident with the longitudinal axis of the spindle while at the same time driving reciprocating linear movement along the same axis. Various drive mechanisms are suitable. For example, those skilled in the art will recognize various combinations of Scotch Yoke mechanisms (e.g., the Scotch Yoke mechanism 16' illustrated in FIG. 11), cams, and gears can be used to produce simultaneous rotary and reciprocating linear movement of the carriage using one or more motors. The drive mechanism is optionally configured to allow adjustment to the angular frequency and/or the frequency of the linear reciprocating motion and/or the maximum linear velocity. For example, the drive mechanism can be configured so a first motor is used to drive rotation and a different motor is used to drive the reciprocating linear motion. Moreover, one or both of the motors can be a variable speed motor to provide the ability to adjust the angular velocity of the rotary movement relative to the maximum speed and/or frequency of the reciprocating linear motion. Further, the drive mechanism is optionally configured to allow adjustment to the amplitude of the linear reciprocating motion. For example, the drive mechanism suitably includes an adjustable length crank arm used in combination with a Scotch Yoke mechanism, as illustrated in FIG. 11.

Figure 12:
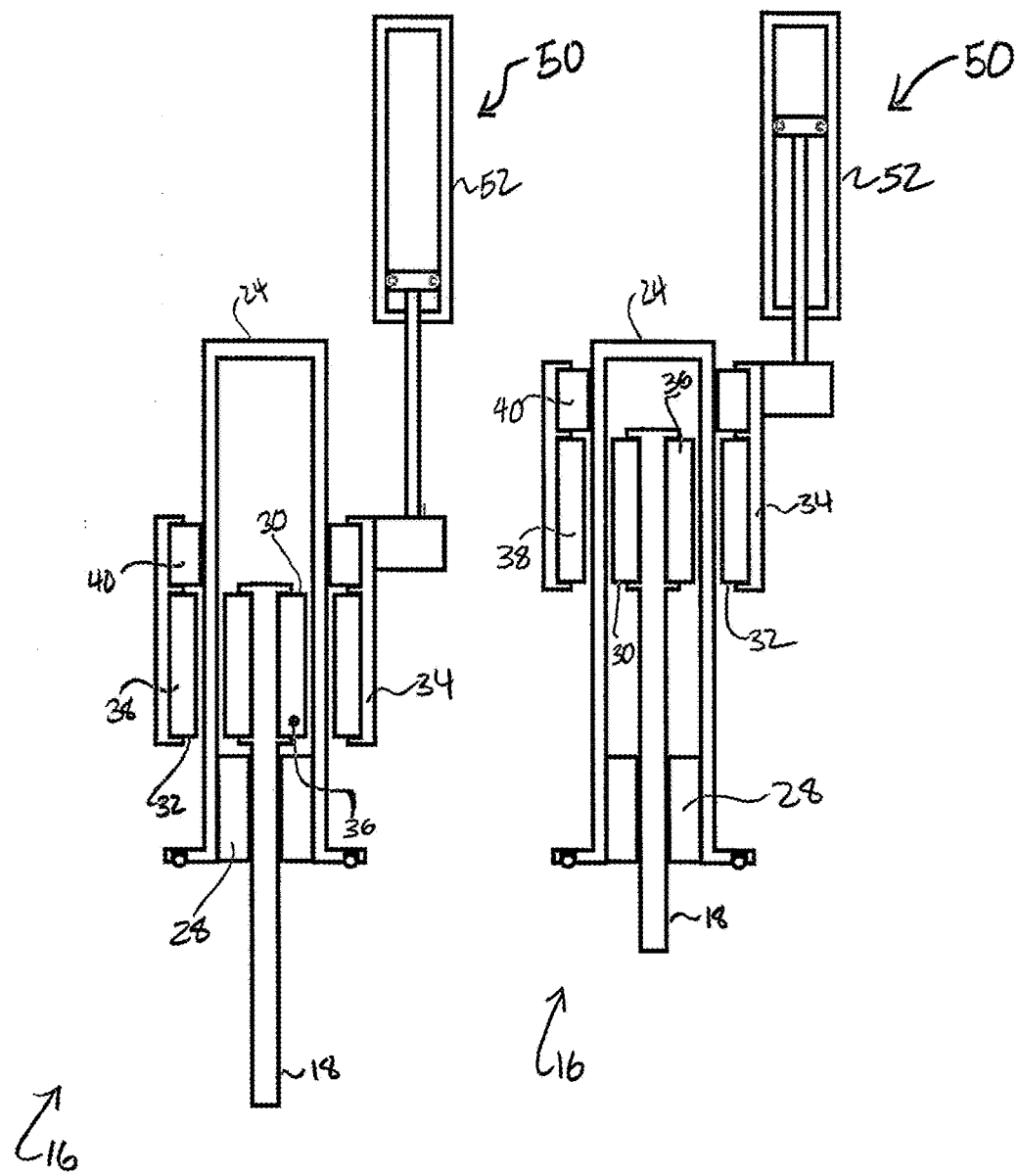
FIG. 12 is a schematic diagram of one embodiment of a drive system that uses a pneumatic cylinder to drive reciprocal linear motion.

FIG. 12 illustrates another embodiment of a drive mechanism 50 that is suitable and which includes a pneumatic cylinder 52 configured to drive reciprocating movement of the carriage 34. For example, a double action cylinder 52 or single action, spring return cylinder can be used. In either case, the direction the cylinder 52 moves, and thus the direction the catalyst basket 14 moves, can be reversed whenever desired (e.g., using a controller to operate a valve that controls operation of the cylinder).

Figure 13:
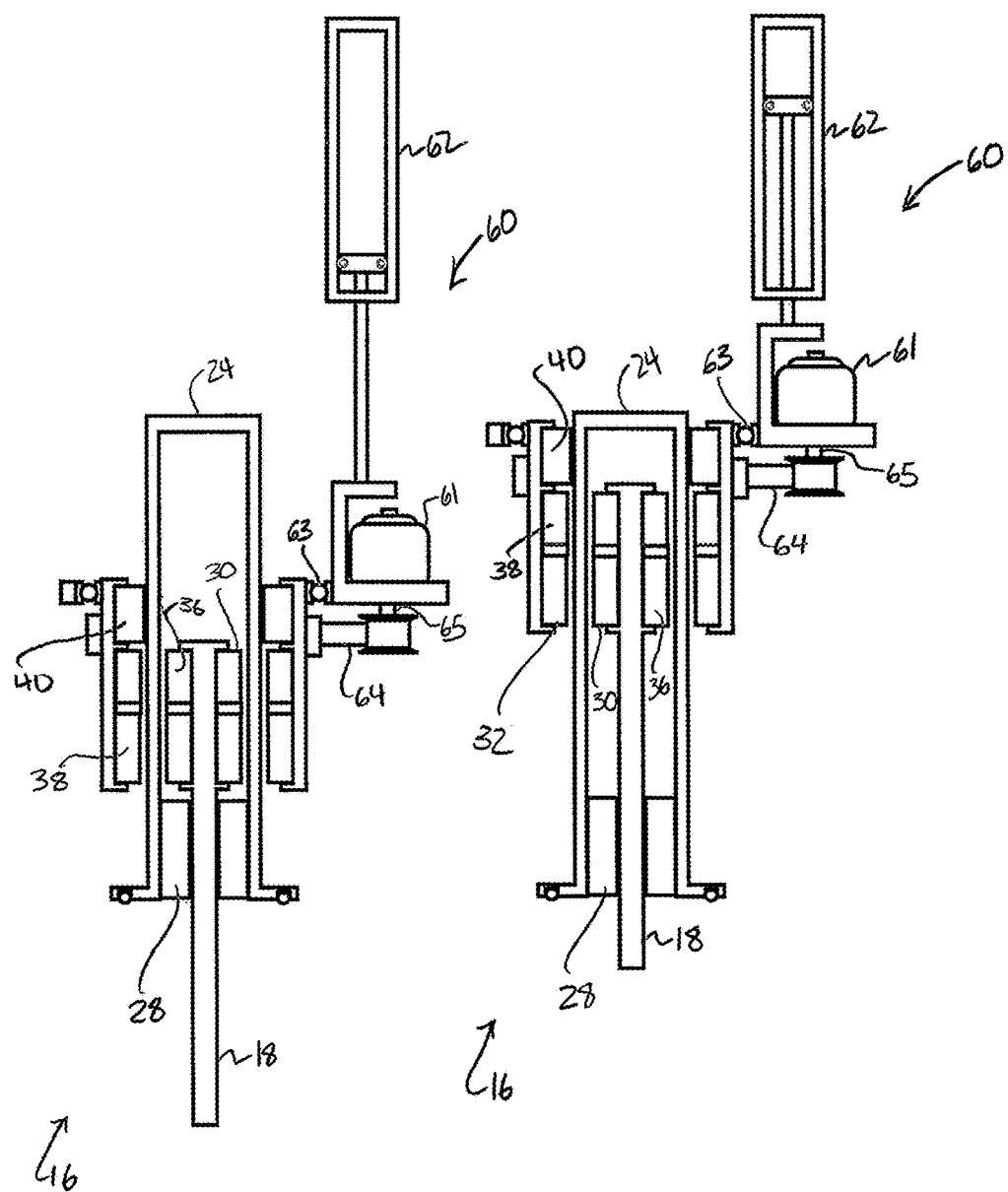
FIG. 13 is a schematic diagram of one embodiment of a drive system that drives reciprocating linear motion and also rotary motion.
Figure 14:
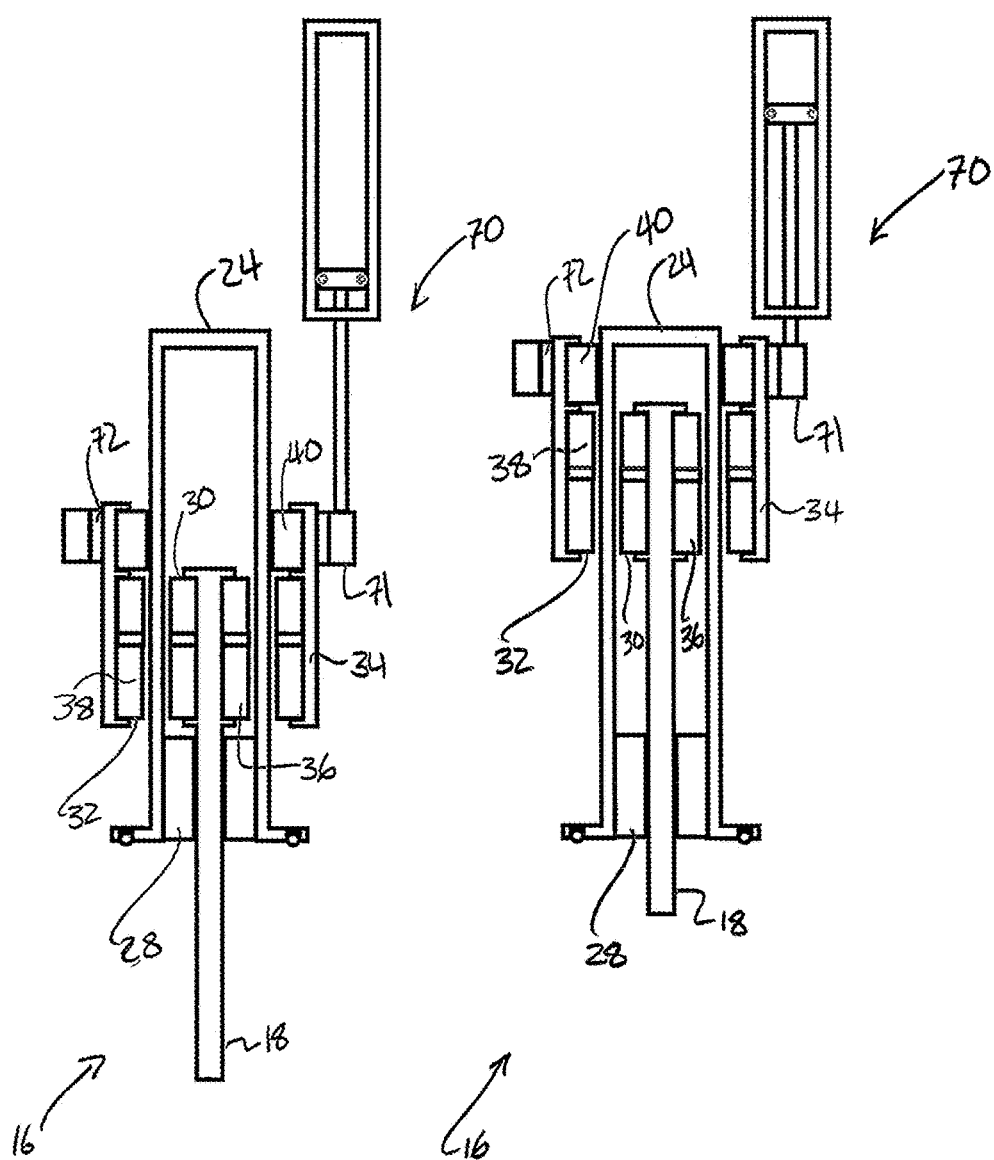
FIG. 14 is a schematic diagram of another embodiment of a drive system that drives reciprocating linear motion and also rotary motion.
Figure 15:
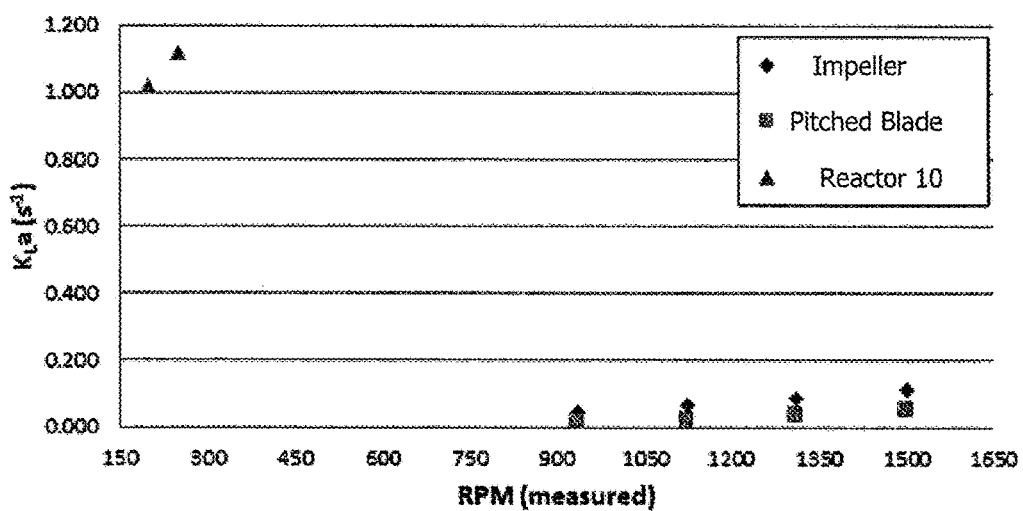
FIG. 15 is a graph comparing that gas liquid mass transfer coefficients of various reactors.

FIGS. 13 and 14 illustrate additional embodiments of suitable drive mechanisms 60, 70 that can produce reciprocating linear motion and rotary motion at the same time. In the embodiment illustrated in FIG. 13, a rotary motor 61 is attached to the output shaft of a reciprocating driver 62 (e.g., linear motor, pneumatic cylinder, or Scotch Yoke mechanism). The rotary motor 61 is secured to the carriage 34 (e.g., by a rotary bearing 63) so the motor and carriage move with one another as the motor is driven back and forth by the linear driver 62. A timing belt 64 or other suitable drive component drivingly connects the rotating output shaft 65 of the motor 61 to the carriage 34 so the rotary motor rotates the carriage. The magnets 38 on the carriage exert forces on the follower that cause the movement of the follower 30 to follow the carriage 34. The drive mechanism 70 in FIG. 14 is substantially the same as the drive system 60 in FIG. 13 except that the rotary motor 61 is replaced with a hollow rotary motor 71. An inner rotor 72 of the motor 71 is hollow and the carriage 34 is secured to the rotor within the central opening of the hollow rotor. Other types of drive systems can also be used without departing from the scope of the invention.

To use the reactor 10 one or more liquid reaction materials are placed in the reactor. One or more gaseous reaction materials are also added to the reactor 10. The level of liquid reaction materials is selected to determine which mode the reactor 10 will operate in: submerged bed, trickle bed, or hybrid. Again, this can be done by adjusting the volume of reaction materials in any particular reactor or by selecting a reactor having a different geometry and/or catalyst basket position. During the reaction, the catalyst basket 14 is driven to rotate while simultaneously being driven to reciprocate along the linear path P (e.g., move up and down along a substantially vertical path). This action drives fluid reaction materials through the catalyst bed in a non-radial direction. For example, liquid reaction materials are suitably driven upwardly through the catalyst bed on the downstroke and is driven downwardly through the catalyst bed on the upstroke. There can also be a radial component to fluid flow through the catalyst bed due to the rotary motion of the catalyst basket 14, however, the action of the catalyst basket substantially prevents formation of stagnation points within the catalyst bed.

The combination of rotary motion and reciprocating linear motion produces substantially higher gas-liquid mass transfer coefficients (KLa) than could be achieved without the combined motion. For example, Table 1 below indicates the gas-liquid mass transfer coefficient achieved using only linear motion of a catalyst basket in a 15.3 mL reactor. In other words, rotary motion for this experiment was 0 rpm.

TABLE 1

Reciprocating Linear Motion Only Data: Gas uptake at 250 PSIG, using 12 grams of IPA and Nitrogen gas

| Linear Speed (m/s) | Frequency (Hz) | Reactor Volume (mL) | Pi (PSIG) | Motor Speed (RPM) | KLa - 15.3 mL (s−1) |
|---|---|---|---|---|---|
| 0.21 | 2.5 | 50 | 250 | 150 | 0.176 |
| 0.28 | 3.3 | 50 | 250 | 200 | 1.108 |
| 0.35 | 4.2 | 50 | 250 | 250 | 1.018 |

Those skilled in the art will recognize the gas-liquid mass transfer coefficients achieved with the reciprocating linear motion (shown in Table 1) are very high compared to those that would be achieved by conventional mixing techniques. For example, as shown in table 2, corresponding data showing the mass transfer coefficients achieved using the same reactor and chemistry but without linear motion and with rotary motion (with two different impellers) shows the pure rotary motion is unable to achieve the relatively high mass transfer coefficients achieved with the reciprocating linear motion.

TABLE 2

Rotary Mixing: Gas Uptake at 250 PSIG, using 20 grams of IPA and Nitrogen

| Mixer Speed (RPM) | Reactor Volume (mL) | Pi (PSIG) | Kla of impeller reactor | Kla of pitched blade reactor |
|---|---|---|---|---|
| 1000 | 50 | 250 | 0.047 | 0.012 |
| 1200 | 50 | 250 | 0.067 | 0.021 |
| 1400 | 50 | 250 | 0.087 | 0.032 |
| 1600 | 50 | 250 | 0.112 | 0.051 |

It is understood that adding rotational movement to the catalyst basket in combination with the reciprocating linear movement will also produce significantly higher mass transfer coefficients than conventional techniques. The ability to achieve high gas-liquid mass transfer coefficients at relatively low RPMs (e.g., from 0 rpm up to about 600 rpm) protects the catalyst materials in the catalyst basket from degradation due to excessive shear forces. FIG. 14 shows a comparison of the mass transfer coefficients for reactions performed in a conventional impeller reactor, a pitched blade reactor, and the reactor 10 at various rotational speeds. The impeller reactor and pitched blade reactor were operated at rotational speeds in excess of 900 RPM, while the reactor 10 was operated at rotational speeds of about 300 RPM or less. As can be seen, the reactor 10 had a significantly higher liquid mass transfer coefficient at lower rotational speeds.

Figure 4:
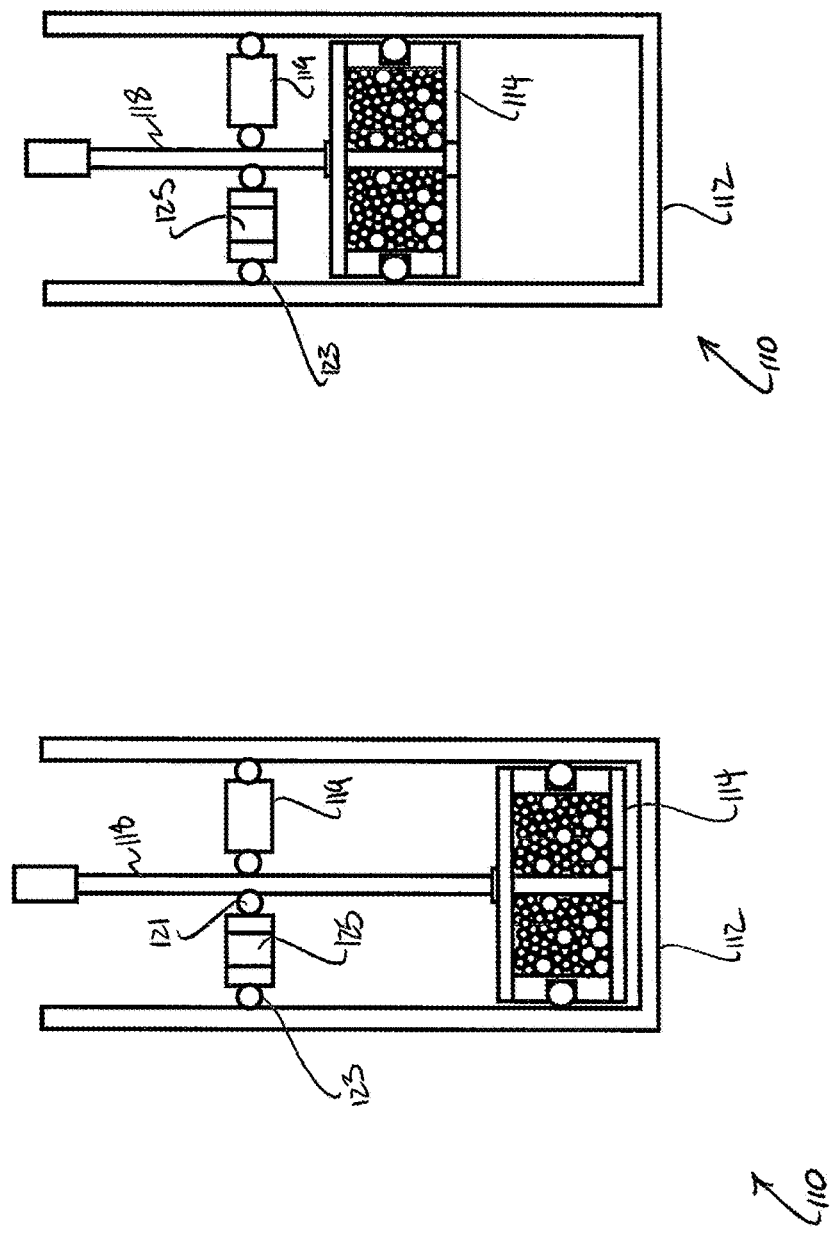
FIG. 4 is a schematic diagram illustrating another embodiment of a reactor of the present invention.

FIG. 4 illustrates another embodiment of a reactor 110 of the present invention. The reactor 110 illustrated in FIG. 4 is constructed and can be operated in substantially the same way as the reactor 10 in FIGS. 1-3, except as noted. Features of the reactor 110 that correspond with features of the reactor 10 are given the same reference number, plus 100. The reactor 110 includes a liquid barrier 119 and a positioned above the catalyst basket 114. The liquid barrier 119 has an opening through which the spindle 118 holding the catalyst basket extends and an O-ring 121 forming a seal between the spindle and the liquid barrier. Another O-ring 123 forms a seal between the liquid barrier 119 and the reactor vessel 112. A gas permeable/liquid impermeable structure 125 is included in the liquid barrier 119 to allow gas to flow through the liquid barrier but limit flow of liquid through the liquid barrier. During operation, this reactor 110 forces liquid upward through the catalyst basket on the downstroke by creating a high pressure zone in a space that is too small to contain all the liquid reaction materials. On the upstroke, the catalyst basket 114 lifts liquid reaction materials until the upper surface of the liquid contacts the liquid barrier. The liquid barrier forces liquid downward through the catalyst bed on the latter part of the upstroke.

Figure 5:
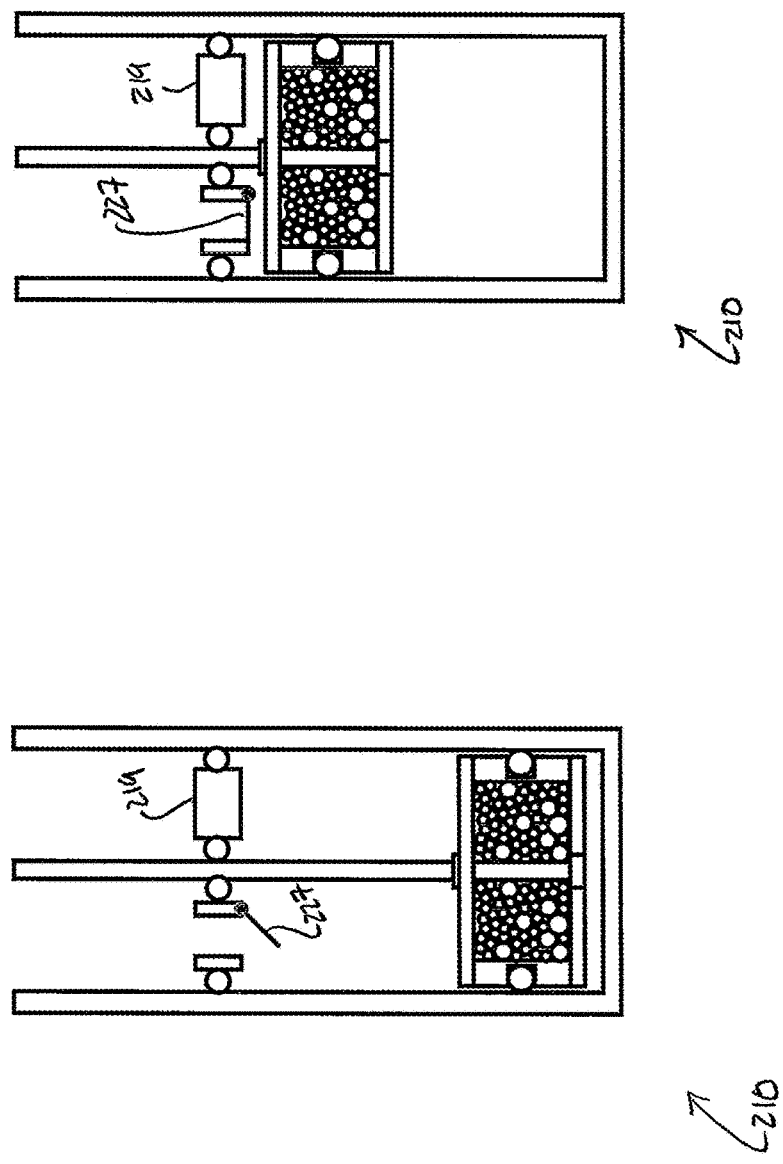
FIG. 5 is a schematic diagram illustrating another embodiment of a reactor of the present invention.

Another embodiment of a reactor 210 of the present invention is illustrated in FIG. 5. This embodiment is substantially identical to the embodiment illustrated in FIG. 4, except that the liquid barrier 219 includes a one-way valve 227 instead of a gas permeable structure 125.

Figure 6:
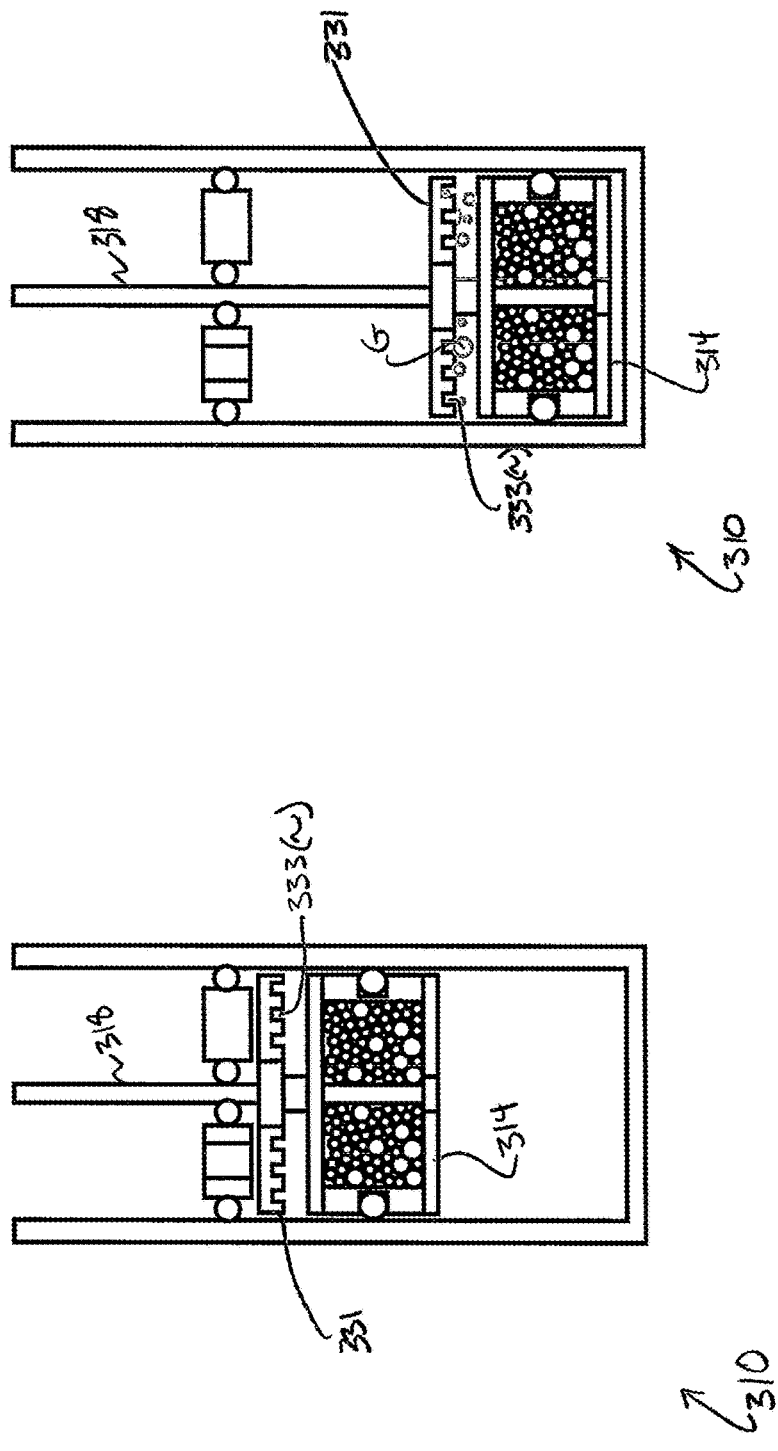
FIG. 6 is a schematic diagram illustrating another embodiment of a reactor of the present invention.

FIG. 6 illustrates still another embodiment of a reactor 310 of the present invention. This embodiment is substantially identical to the embodiment illustrated in FIG. 4, except as noted. Features of the reactor 310 that correspond with features of the reactor 110 are given the same reference number, plus 200. The spindle 318 in this embodiment supports a gas trapping plate 331 above the catalyst basket 314. The gas trapping plate 331 has one or more recessed areas 333 in its underside. The gas trapping plate 331 moves up and down with the up and down reciprocating movement of the catalyst basket 314. There is no seal, however, between the gas trapping plate 331 and the reactor vessel 312. Thus, fluid reaction materials can flow around the gas trapping plate 331. The gas trapping plate 331 is suitably positioned at an elevation on the spindle 318 that will result in repeated submersion of the gas trapping plate in the liquid reaction materials on the downstroke followed by withdrawal of the gas trapping plate on the upstroke. Gas bubbles G are trapped by the receptacles in the gas trapping plate as the plate is submerged into the liquid reaction materials on the downstroke. This can enhance mixing gaseous reaction materials into the liquid reaction materials.

Figure 7:
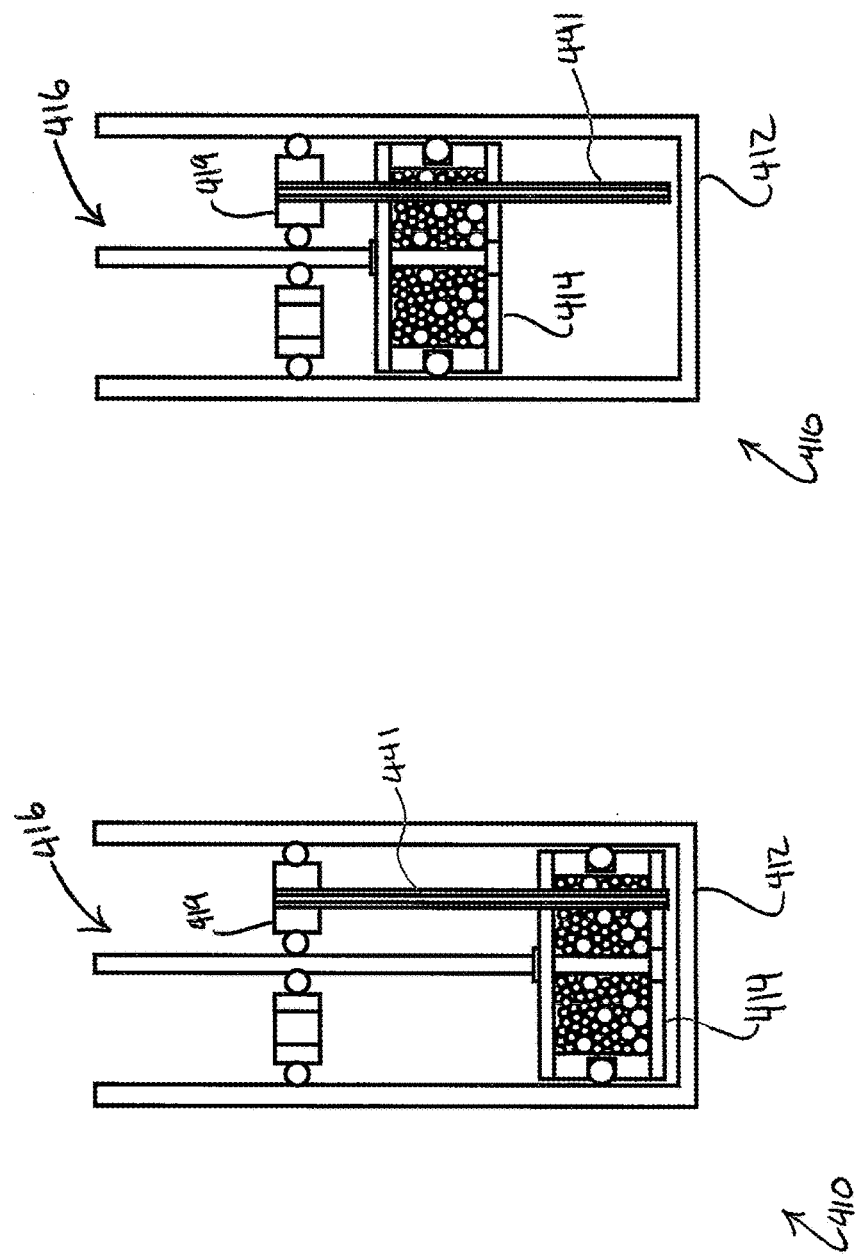
FIG. 7 is a schematic diagram illustrating another embodiment of a reactor of the present invention.

FIG. 7 illustrates yet another embodiment of a reactor 410 of the present invention. This embodiment is substantially identical to the embodiment illustrated in FIG. 4, except as noted. Features of the reactor 410 that correspond with features of the reactor 110 are given the same reference number, plus 300. In this embodiment, a dip tube 441 extends through the liquid barrier 419 and the catalyst basket 414. The liquid barrier 419 and dip tube 441 are held at a fixed elevation in the reactor and do not move with the reciprocating linear motion of the catalyst basket 414. The drive system 416 is suitably configured to produce linear reciprocating motion of the catalyst basket 414 without any rotation (i.e., rotation is suitably 0 rpm). The dip tube 441 includes a gas permeable liquid seal (not shown; e.g., a porous membrane) that allows gas to flow through the dip tube but blocks flow of liquid through the dip tube. This reactor is configured to mix gas into a pool of liquid reaction materials at the bottom of the reaction vessel 412. In particular, the low pressure zone created under the catalyst basket 414 on its upstroke draws gas from above the liquid barrier down through the dip tube into the liquid at the bottom of the reactor 410.

FIG. 8 illustrates still another embodiment of a reactor 510 of the present invention. This embodiment is substantially similar to the embodiment illustrated in FIG. 4, except as noted. Features of the reactor 510 that correspond with features of the reactor 110 are given the same reference number, plus 400. One difference between the reactor 110 illustrated in FIG. 4 and the reactor 510 illustrated in FIG. 8 is that the reactor in FIG. 8 has an adjustable volume catalyst basket 514. In particular, the elevation of a porous sheet 551 forming the top of the catalyst basket 514 is adjustable. There are various different ways to allow for height adjustments. For example, the reactor system suitably includes a set of spacers having multiple different sizes that can be positioned to block upward movement of the catalyst basket. Thus, the volume of the catalyst basket can be decreased by using a larger spacer and/or increased by using a smaller spacer. The ability to adjust the volume of the catalyst basket 514 allows the catalyst particles to be clamped in place by the top 551 of the catalyst basket to reduce grinding of particles against one another. In turn, the ability to reduce particle grinding can reduce the undesirable generation of fine catalyst particles. If desired, the volume of the catalyst basket 514 can be decreased so that it can hold only a single layer of catalyst particles, as illustrated in the right side of FIG. 8.

Figure 9:
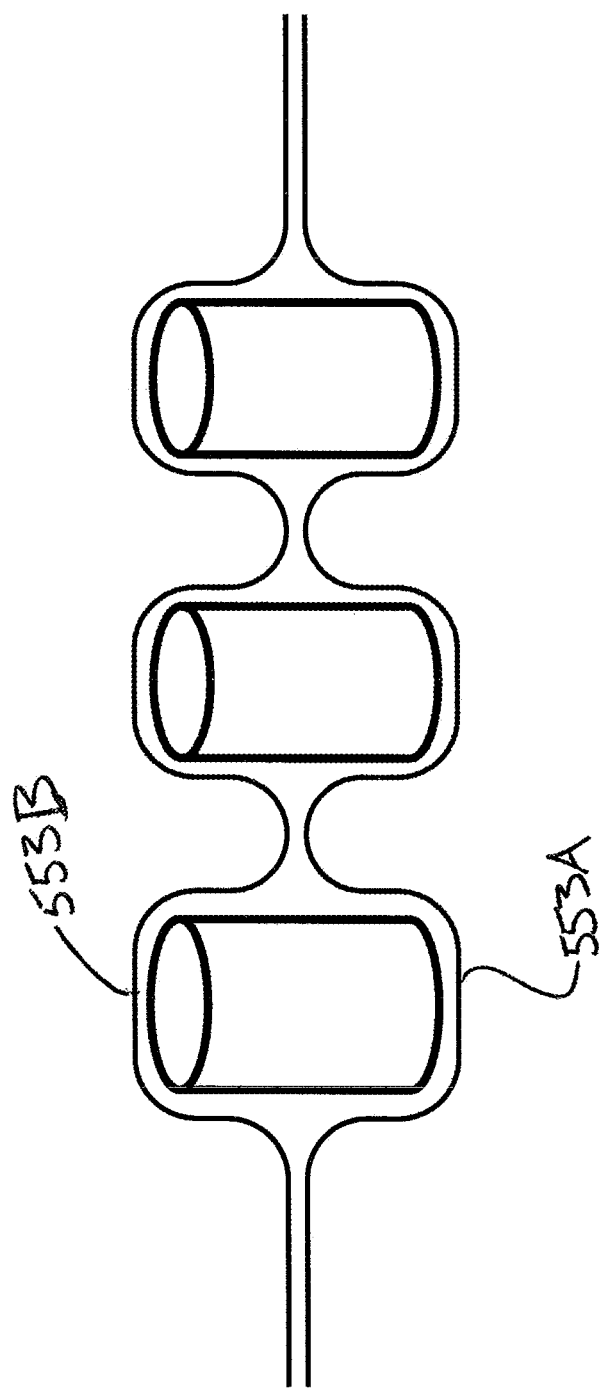
FIG. 9 is a schematic diagram illustrating one embodiment of a catalyst holder of the present invention.

Moreover, the right side of FIG. 8 illustrates the reactor being used with a catalyst holder 514 that is configured to hold a plurality of catalyst particles so the catalyst particles remain spaced apart from one another. In particular, a compliant porous particle locking sheet 553 is inserted in the catalyst basket 514 above the single layer of catalyst particles. A plurality of pockets are formed in the bottom of the locking sheet 553. The pockets are suitably sized so no more than a single catalyst particle can fit into each pocket. As illustrated in FIG. 9, a pair of particle locking sheets 553A, 553B can be arranged so at least some of the pockets of the respective sheets are in registration with one another so they collectively hold the particles spaced apart from one another. If desired, multiple particle locking sheets can be stacked on top of one another to hold multiple layers of catalyst particles so that substantially every catalyst particle in the catalyst basket is spaced from substantially every other catalyst particle. One example, of a suitable particle locking sheet can be formed by embossing dimples in a thin, compliant, highly-porous stainless steel mesh disk. The size of the dimples/pockets can be varied to suit the size of the catalyst particles.

Figure 10:
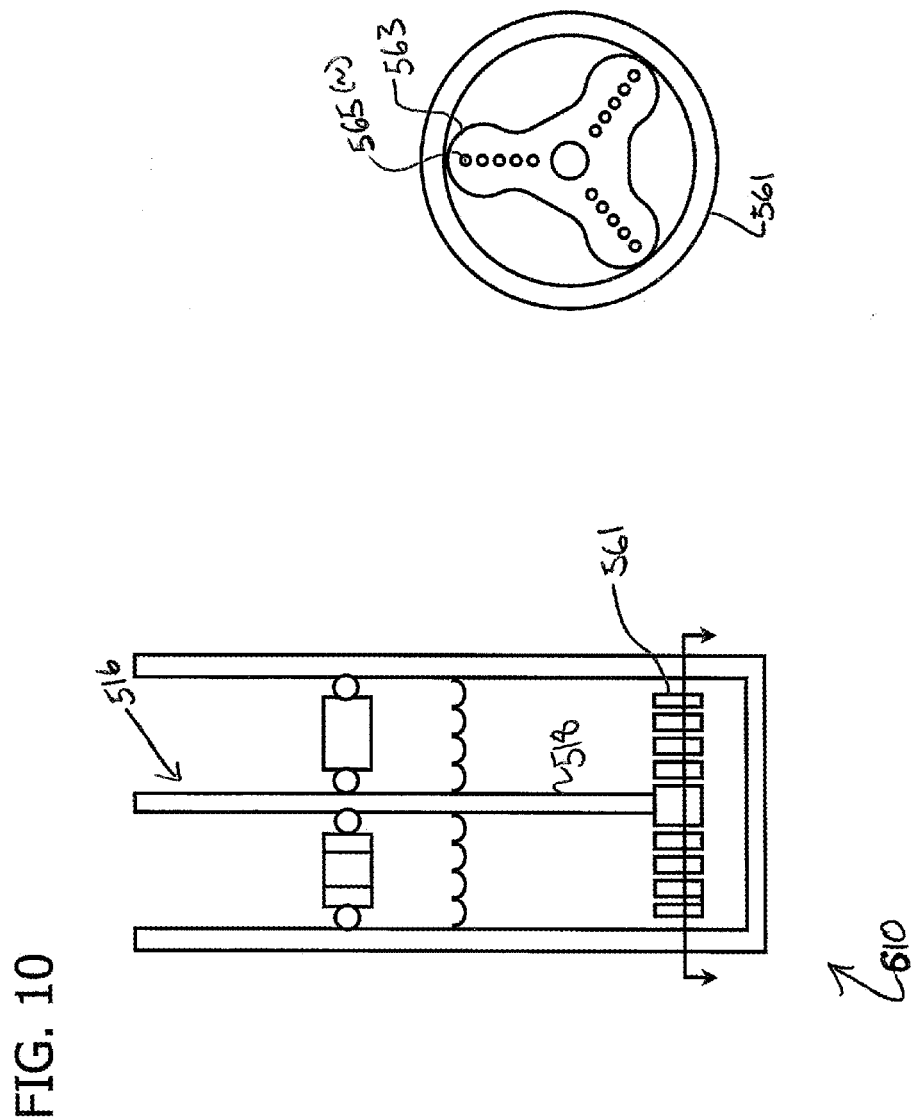
FIG. 10 is a schematic diagram illustrating yet another embodiment of a reactor of the present invention.

FIG. 10 illustrates another embodiment of a reactor 610 of the present invention. This embodiment is substantially similar to the embodiment illustrated in FIG. 4, except as noted. Features of the reactor 610 that correspond with features of the reactor 110 are given the same reference number, plus 500. One difference is that the catalyst basket is replaced with an impeller 561. The drive system 516 described above is connected to the impeller 561 in a manner similar to the catalyst basket 114 so the drive system drives linear motion of the impeller. The drive system 516 optionally also drives rotation of the impeller 561. The impeller 561 has three lobes 563 spaced equi-angularly about central portion which is connected to the drive system by a shaft 518. There are optionally a plurality of openings 565 in the impeller. As illustrated in FIG. 10, for example, a series of small openings 565 is located within each lobe 563 of the impeller. The openings 565 allow fluid (e.g., gas and liquid) to pass through the impeller lobes, which may be desirable to create additional eddies and/or break up larger gas bubbles into smaller gas bubbles to facilitate mass transfer between gas and liquid phase(s). The reactor 510 illustrated in FIG. 10 is suitable for conducting reactions in which catalyst particles are suspended in the liquid reaction materials. In particular, the drive system 516 can move the impeller repeatedly up and down through the liquid reaction materials to maintain the catalyst particles in a suspended condition.

When introducing elements of the apparatus and methods described and illustrated herein, the articles "a", "an", "the" and "said" are intended to mean that there are one or more of the elements. The terms "comprising", "including" and "having" and variations thereof are intended to be inclusive and mean that there may be additional elements other than the listed elements. Moreover, the use of "forward" and "rearward" and variations of these terms, or the use of other directional and orientation terms, is made for convenience, but does not require any particular orientation of the components.

As various changes could be made in the above without departing from the scope of the invention, it is intended that all matter contained in the above description and shown in the accompanying drawings shall be interpreted as illustrative and not in a limiting sense.

The invention claimed is:

1. A reactor for conducting laboratory reactions, the reactor comprising:
   a reaction vessel,
   a catalyst basket in the reaction vessel, the catalyst basket being sealed against an internal sidewall of the reaction vessel, and
   a drive system configured to drive reciprocating linear movement of the catalyst basket.

2. A reactor as set forth in claim 1 wherein the drive system is further configured to drive rotary motion of the catalyst basket and said linear reciprocating movement at the same time.

3. A reactor as set forth in claim 2 wherein the drive system is configured to rotate the catalyst basket at a speed in the range of 0 rpm to 600 rpm.

4. A reactor as set forth in claim 2 wherein the drive system is configured to drive the catalyst basket so the maximum linear velocity is in the range of about 0 to about 1.0 m/s.

5. A reactor as set forth in claim 2 wherein the drive system is configured to adjust a ratio of an angular velocity of the catalyst basket to a linear velocity of the catalyst basket to adjust the pitch of a helical path of the catalyst basket.

6. A reactor as set forth in claim 1 wherein the drive system is configured to drive the linear movement of the catalyst basket according to a harmonic oscillation.

7. A reactor as set forth in claim 1 wherein the drive system is configured to drive reciprocating linear movement of the catalyst basket at a frequency in the range of about 1 Hz to about 10 Hz.

8. A reactor as set forth in claim 1 wherein the reactor is configured to drive flow of reaction materials through the catalyst basket in a non-radial direction.

9. A reactor as set forth in claim 1 wherein the catalyst basket divides the reaction vessel into two different zones and limits flow of reaction materials between the zones except by flow of the reaction materials through the catalyst basket.

10. A reactor as set forth in claim 1 wherein the drive system comprises a spindle connected to the catalyst basket for driving movement of the catalyst basket, the reactor further comprising a liquid barrier that is substantially impermeable to liquid and permeable to gas, the liquid barrier having an opening for receiving the spindle and an O-ring at the opening forming a seal between the liquid barrier and the spindle.

11. A reactor as set forth in claim 10 further comprising a gas trapping plate between the liquid barrier and the catalyst basket, the gas trapping plate being connected to the spindle so that the drive system moves the gas trapping plate in a reciprocating linear movement corresponding to the reciprocating linear movement of the catalyst basket.

12. A reactor as set forth in claim 1 wherein the drive system comprises a spindle connected to the catalyst basket for driving movement of the catalyst basket, the reactor further comprising a liquid barrier that is substantially impermeable to liquid and a one-way valve installed in the liquid barrier, the liquid barrier having an opening for receiving the spindle and an O-ring at the opening forming a seal between the liquid barrier and the spindle.

13. A reactor as set forth in claim 1 wherein the drive system comprises a spindle connected to the catalyst basket for driving movement of the catalyst basket, the reactor further comprising a liquid barrier that is substantially impermeable to liquid, the liquid barrier having an opening for receiving the spindle and an O-ring at the opening forming a seal between the liquid barrier and the spindle, the reactor further comprising a dip tube positioned to extend through the liquid barrier and the catalyst basket.

14. A reactor as set forth in claim 13 wherein the reactor is configured so gas can flow from a first zone in the reactor through the dip tube into a second zone in the reactor on the opposite side of the catalyst basket in response to linear movement of the catalyst basket.

15. A reactor as set forth in claim 1 wherein the catalyst basket is configured to hold catalyst particles so the catalyst particles are clamped in place.

16. A reactor as set forth in claim 1 wherein the catalyst basket is configured to hold a plurality of catalyst particles so the catalyst particles are remain spaced from one another.

17. A reactor as set forth in claim 15 wherein the catalyst basket comprises a porous locking sheet having a plurality of pockets therein for holding catalyst particles in spaced relation from one another.

18. A reactor for conducting laboratory reactions, the reactor comprising:
 a reaction vessel,
 a catalyst basket in the reaction vessel, and
 a drive system configured to drive reciprocating linear movement of the catalyst basket, the drive system comprising a spindle connected to the catalyst basket and a magnetic coupling drivingly connecting the spindle to a motor.

19. A reactor for conducting laboratory reactions, the reactor comprising:
 a reaction vessel,
 a catalyst basket in the reaction vessel, the catalyst basket is configured to hold a plurality of catalyst particles so the catalyst particles are remain spaced from one another, the catalyst basket comprising a porous locking sheet having a plurality of pockets therein for holding catalyst particles in spaced relation from one another, and
 a drive system configured to drive reciprocating linear movement of the catalyst basket.

* * * * *